United States Patent [19]

Mayer

[11] Patent Number: 5,053,116
[45] Date of Patent: Oct. 1, 1991

[54] DEVICE FOR HUMIDIFYING GASES WITHOUT CHANGING OXYGEN CONTENT

[75] Inventor: Daniel W. Mayer, St. Paul, Minn.

[73] Assignee: Modern Controls, Inc., Minneapolis, Minn.

[21] Appl. No.: 509,365

[22] Filed: Apr. 16, 1990

Related U.S. Application Data

[63] Continuation-in-part of Ser. No. 437,629, Nov. 17, 1989, Pat. No. 4,973,395.

[51] Int. Cl.⁵ .............................................. G01N 27/26
[52] U.S. Cl. .............................. 204/406; 204/153.16; 204/411
[58] Field of Search ..................... 204/406, 411, 153.16

[56] References Cited

U.S. PATENT DOCUMENTS 3,223,597 12/1965 Hersch ........................... 204/431 X
4,085,024 4/1978 Lawson ........................... 204/432

Primary Examiner—John F. Niebling
Assistant Examiner—William T. Leader
Attorney, Agent, or Firm—Paul L. Sjoquist

[57] ABSTRACT

A device for humidifying gases without oxygen comprised of a gas conduit for passing the gases through the device to be humidified having a portion of the conduit being permeable to water but a barrier to electrolytes. The portion of the gas conduit is positioned closely adjacent the anode of a galvanic cell also having a cathode. A reservoir is provided for placement of the galvanic cell and the portion of the gas conduit therein which is at least partially filled with an electrolyte solution.

19 Claims, 3 Drawing Sheets

Fig. 7A

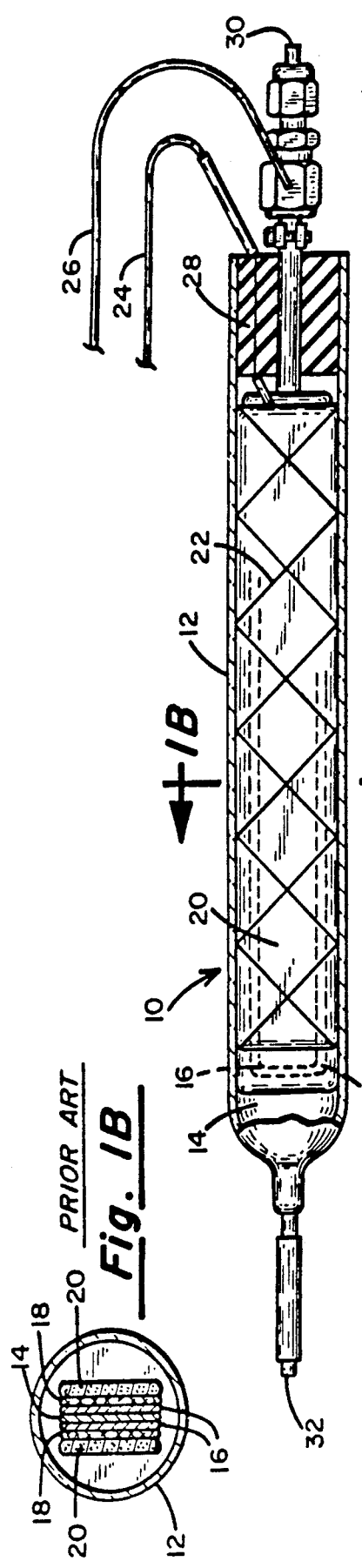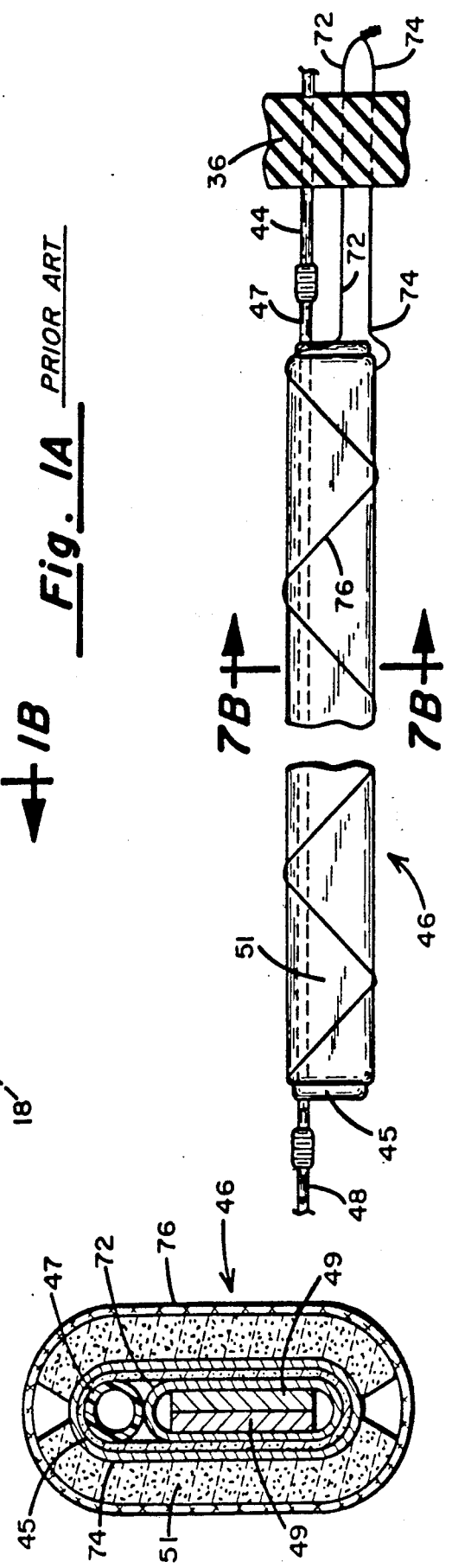

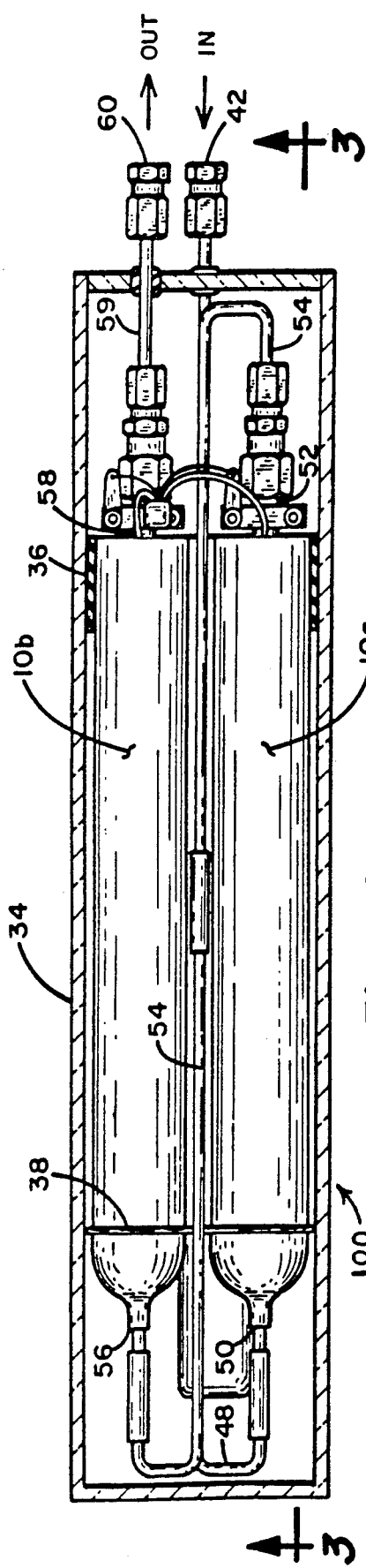
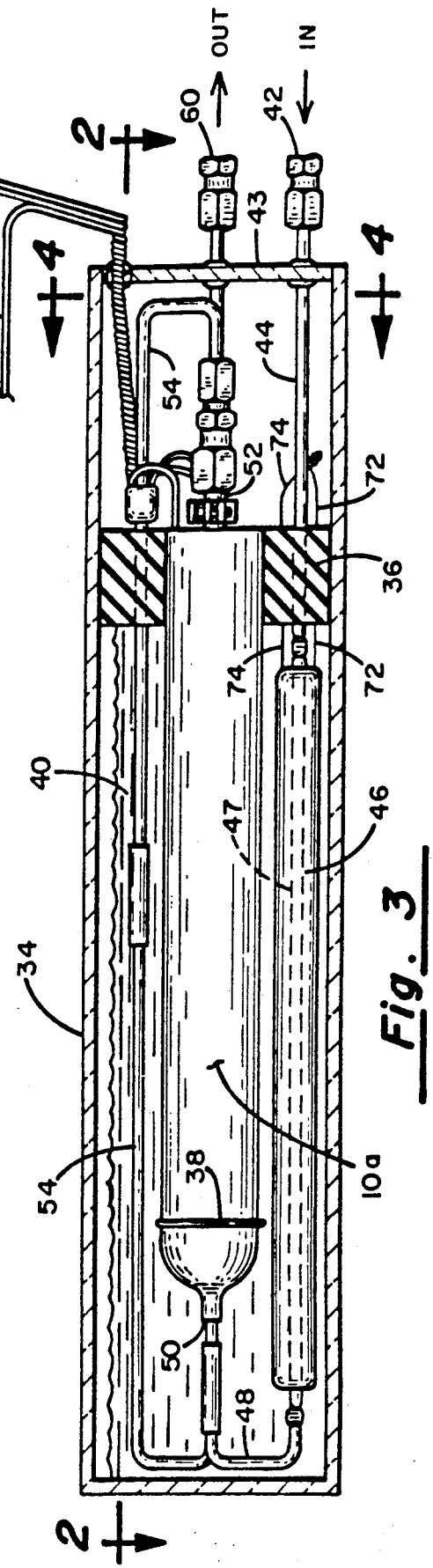

DEVICE FOR HUMIDIFYING GASES WITHOUT CHANGING OXYGEN CONTENT

BACKGROUND OF THE INVENTION

This invention is a continuation-in-part of U.S. Pat. application Ser. No. 437,629, filed on Nov. 17, 1989 for a Humidified High Sensitivity Oxygen Detector by William N. Mayer and Daniel W. Mayer and assigned to Modern Controls, Inc. of Minneapolis, Minn.

The present invention relates to a device for humidifying gases without the introduction of oxygen with the aid of a galvanic cell and a partially permeable conduit.

The parent invention referenced above comprises an oxygen sensor of the galvanic cell type having a pair of galvanic cells. The cells are housed within a single housing with a test gas conduit having a water permeable section. The galvanic cells are electrically connected to provide respective output voltages which may be subtractively coupled to eliminate noise signals thereby providing an output voltage signal which is wholly representative of oxygen content of the test gas going through the sensor.

Known prior art includes U.S. Pat. No. 3,223,597, Hersch, which discloses a galvanic cell construction which includes a chemically reducing anode, a nonconductive thin porous electrolyte-retentive diaphragm in intimate contact with at least one surface of the anode, a cathode comprising a thin porous conductive sheet in intimate contact with the surface of the diaphragm opposite to the surface in contact with the anode, and an aqueous electrolyte contained in the porous diaphragm. The pores of the cathode are only partially filled with electrolyte, and the cathode is chemically nonreactive to the electrolyte, the anode being incapable of evolving hydrogen upon being circuited with the cathode. The total volume of electrolyte is less than the combined total pore volume of the cathode, diaphragm and anode, so that only a minor portion of the pores of the cathode become wetted while a major portion of the pores of the cathode never become filled. This construction results in an electrode assembly whereby only the surface of the cathode which is in intimate contact with the diaphragm is wetted, and the top surface and major portion of the pores of the cathode remain substantially dry.

U.S. Pat. No. 4,085,024, Lawson, discloses essentially the same electrode assembly as the Hersch patent, using a particular construction technique for interconnecting the elements of the cell and sealing it inside an oxygen-free envelope.

The foregoing constructions are critically dependent upon the concentration and quantity of electrolyte contained within the cell and the operating temperature of the cells. Further, the sensitivity or operability of such cells degrades with time, as the water content of the electrolyte becomes dissipated from the cell.

There is a need for a galvanic cell-type device for humidifying gases without introducing or absorbing oxygen in the gases. Such a device should have a long life, be unaffected by temperature and predictably humidify dry air flowing therethrough, and also have a reasonably good response to dynamic changes in the gases being measured.

There is a need for a humidifier which has a relatively large reservoir of electrolyte in order to provide for a long and useful life of the humidifier, but which has a very small internal gas volume in order to provide good dynamic response to changes in oxygen content in the incoming gases. Further, there is a need for a humidifier which does not change the oxygen concentration of the input gases more than about 35-100 parts per trillion.

There is a further need for a device for humidifying gases which will maintain the relative humidity in the range of 60%-90%, for use in conjunction with a galvanic cell sensor, to provide sensor operation in its optimum range.

The present invention meets the foregoing needs and adequately humidifies gases in temperate ranging from 10°-60° C., and at gas flow rates ranging from 1-20 cc/min.

SUMMARY OF THE INVENTION

A device for humidifying gases without introducing oxygen is comprised of a gas conduit for passing the gases through the device to be humidified having a portion of the conduit being permeable to water but a barrier to electrolytes. The portion of the gas conduit is positioned closely adjacent the anode of a galvanic cell also having a cathode. A reservoir is provided for placement of the galvanic cell and the portion, which is at least partially filled with an electrolyte solution, of the gas conduit therein.

It is a principal object of the present invention to provide a device for humidifying gases without introducing or absorbing oxygen in a novel manner by way of a permeable gas conduit adjacent to a galvanic cell in an electrolyte solution.

Another object of the present invention is to provide a device for humidifying gas flowing at the rate of 1-20 cc/min. therethrough to a certain percentage of relative humidity in the range of 60%-90%.

It is a further object of the present to provide a device for humidifying gases that is unaffected by temperatures ranging from 10°-60° C.

It is a further object of the present invention to provide a device for humidifying gases that will have a long operating life and a fast response time to dynamic changes which occur in the gas flow therethrough.

BRIEF DESCRIPTION OF THE DRAWINGS

The foregoing and other objects and advantage of the present invention will become apparent from the following specification and claims, and with reference to the drawings, in which:

FIG. 1A shows a galvanic cell of the type known in the prior art.

FIG. 1B shows a cross-section view taken along the lines 1—1 of FIG. 1A.

FIG. 2 shows a top sectional view of the humidified high-sensitivity oxygen detector of the parent application utilizing the present invention taken along the lines 2—2 of FIG. 3.

FIG. 3 shows an elevational and sectional view of the oxygen detector incorporating the present invention taken along the lines 3—3 of FIG. 2.

FIG. 7A shows a side elevation view of the present invention.

FIG. 7B shows a cross-section view taken along the lines 7B—7B of FIG. 7A.

DESCRIPTION OF THE PREFERRED EMBODIMENT

Figure 4:
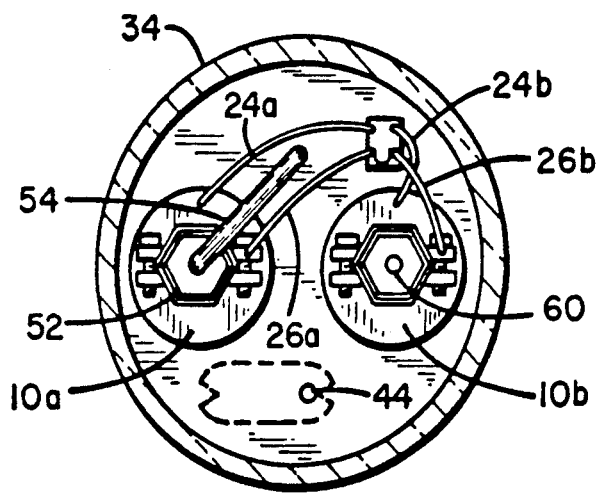
FIG. 4 shows a cross-section view taken along the lines 4—4 of FIG. 3.

The present device for humidifying gases without introducing or absorbing oxygen is believed to have multiple purposes and applications. For illustrative reasons only, the device is described in detail herein as used with the oxygen detector of the above referenced parent application. Thus, the oxygen detector will be described first to place the present invention in context of one known use among many believed possibilities.

Referring first to FIGS. 1A and 1B, a galvanic cell of the type known in the prior art is illustrated, in several views. Galvanic cell oxygen detector 10 includes a sealed gas envelope 12 which has an inlet 32 for connecting to a source of test gas, and an outlet 30 for exhausting the test gas from the cell 10. The constructional details of the elements within cell 10 may be similar to the construction described in Hersch Patent No. 3,223,597; Lawson Patent No. 4,085,024 or other prior art devices. The interior cell components preferably include a central anode blade 14 which is electrically coupled to an anode wire 26 which passes outside of the cell 10. Anode blade 14 has an anode element 16 adjacent each of its flat surfaces, and a, porous layer 18 outwardly adjacent each of the anode elements 16. The entire structure may be bound together by nylon thread 22 to form a tight assembly, and a cathode wire wrap 28 is wound about the porous layers 18 and in electrical contact with the outside cathode layers 20. The cathode wire wrap 28 is electrically connected to a cathode wire 24 which passes outside of the cell 10. The porous layer 18 is typically impregnated with an electrolyte.

The oxygen detector 100 utilizes two galvanic cells of the general type described above, in a construction to be hereinafter described. The galvanic cells are hereinafter referred to as cell 10a, and cell 10b.

FIG. 2 shows a top view of the oxygen detector 100 in partial cross section, taken along the lines 2—2 of FIG. 3. FIG. 3 shows an elevation view of the invention in partial cross section, taken along the lines 3—3 of FIG. 2. Galvanic cells 10a and 10b are sealed within enclosure 34 by plug 36. They are supported relative to one another by a spacer 38, which also supports cells 10a and 10b relative to the inside of enclosure 34. The inside of enclosure 34 may be partially filled with an electrolyte solution 409, preferably including a 12.5 weight percentage (WT%) solution of potassium hydroxide (KOH). It is desirable to nearly completely fill the sealed interior of the enclosure 34 with electrolyte 40.

An inlet 42 is adapted for coupling to a source of test gas, and is coupled to a gas conduit 44 which passes through outer wall 43 of enclosure 34. Gas conduit 44 sealably passes through plug 36 and is coupled to the gas humidifier 46 of the present invention.

Humidifier 46 has the characteristic that it is permeable to water, but includes an interior passageway through tube or conduit 47, which is a barrier to KOH; it is also chemically resistant to KOH. Humidifier 46 also contains an oxygen getter to remove any trace amounts of oxygen which may accumulate inside sealed enclosure 34, particularly in the KOH solution.

The output of humidifier 46 is connected to conduit 48, which is connected to an inlet 50 of galvanic cell 10a. Galvanic cell 10a has an outlet 52 coupled to a further conduit 54 outside of the sealed portion of enclosure 34. Conduit 54 sealably passes through plug 36, and is co connected to an inlet 56 of galvanic cell 10b. Galvanic cell 10b has an outlet 58 which is coupled to a conduit 59 which passes through the outer wall 43, and is connected to an outlet coupling 60, adapted for connection to an exhaust circuit.

Humidifier 46 of the present invention is shown in greater detail in FIGS. 7A and 7B, wherein FIG. 7B shows a cross section of humidifier 46, taken along the lines 7B—7B of FIG. 7A. Humidifier 46 incorporates a layered structure which is arranged to form a galvanic cell, and permeable tube 47 is positioned along an anode edge of this galvanic cell. The galvanic cell may be formed of a plurality of layers of materials, in a manner similar to that described in Hersch Patent No. 3,223,597.

For example, an interior anode is comprised of two sheets of material 49 which may be made from a cadmium compound material. The anode may be made from an oxidizable material from the group including cadmium arsenic, bismuth, anitimony, lead an ferrous hydrate. A metal wire 72 is tightly wrapped about the interior anode, and one end of wire 72 is brought out for subsequent connection. Permeable tube 47 is laid along an edge of anode 49, and an intermediate porous layer or diaphragm 45 is wrapped about the tube 47 and anode 49. A second metal wire 74 is wrapped about porous layer 45, and a one end of wire 74 is brought out for subsequent connection. Finally, an exterior cathode layer 51, which may be formed into sections, is laid over the porous layer and a nylon wrap 76 is wrapped about cathode layer 51. The cathode layer may be made from a reducible material from the group including silver, gold, carbon, graphite, platinum, copper and iridium. An end of wire 74 is electrically connected to an end of wire 72, effectively short circuiting the anode and cathode together. The electrical connection between the ends of wires 72 and 74 is made outside of the sealed interior of enclosure 34.

Permeable tube 47 is a water permeable membrane which is chemically resistant to KOH, and which permits the controlled absorption of water into the gas flow which passes through tube 47. A material which has been found suitable for use in this purpose is a perfluorinated membrane made from a fluorocarbon copolymer of a particular chemical composition; suitably a copolymer of tetrafluoroethylene and a vinyl sufonyl fluoride. This member is sold under the trademark NAFION, and is manufactured by E. I. Dupont de Nemours & company of Wilmington Del.

The NAFION tube 47 is placed closely adjacent the anode 49 of humidifier 46, which serves as an oxygen getter, to reduce the oxygen is the vicinity of tube 47. Therefore, the water passing through the permeable walls of tube 47 is introduced into the test gas stream without introducing extraneous oxygen into the test gas stream. The inherent action of the galvanic cell which is formed as a part of humidifier 46 causes oxygen molecules to be absorbed into the cell, chemically reducing the cadmium anode to a cadmium hydroxide material, and therefore the oxygen is depleted from the immediate vicinity of permeable tube 47. Testing has shown that the region of lowest possible oxygen is the region immediately adjacent anode 49, and therefore tube 47 is positioned along an edge of anode 49.

Because of the characteristics of the NAFION tubing, and the concentration of KOH, the test gas which passes into the device through inlet 42 will be maintained at a constant relative humidity. The humidifier 46, including the NAFION tubing, is preferably wholly immersed in KOH (12.5 WT%), and a dry test gas passing through the tubing in volume flow rates of approximately 20 cc/minute will inherently develop a relative humidity of about 80% (80% RH).

This relative humidity will be constantly maintained throughout the passage of the gas through the galvanic cells 10a and 10b, thereby tending to replenish water which would otherwise be drawn from the device over extended periods of use. If the test gas passing into the inlet of the device has a relative humidity of greater than about 80% RH, the concentration of KOH and the permeability of the NAFION tubing will cause water to pass outwardly through the tubing, thereby depleting the humidity of the gas to about 80% RH.

It can therefore be seen that the presence of the NAFION tubing immersed in a predetermined concentration of KOH tends to create a constant relative humidity under all conditions of dryness of the test gas input. This phenomena aids in the stability of oxygen test measurements, by subjecting all forms of test gas to approximately the same relative humidity during the measurement process performed by the oxygen detector 10.

The relative humidity of a gas can be varied and is inversely related to the KOH concentration. That is, a 5 WT% (weight percentage) will give a 95 %RH; a 10 WT% will give an 89 %RH; a 20 WT% will give 68 %RH; and a 30 WT% will give a 38 %RH, approximately.

It has also been found where the air flow (cc/min (dry)) is increased, the NAFION tube 47 should similarly be increased in length. For flows from 1 to 21 cc/min (dry), a tube length of nine inches or longer is appropriate where the tube's diameter is approximately 1/16 of an inch. With tube lengths in excess of 9 inches, the percent RH becomes relatively constant.

In one example, a gas humidifier 46 having 250 ml. of KOH in the reservoir generates 60%–80% RH for approximately 600 to 700 days when operating at 20° C., at gas flow rates of 10 cc/min. When operating at colder temperatures, such as 0° C., the humidifier 46 may last up to 7 years. Operating the same humidifier 46 at 50° C. may shorten the life of the humidifier 46 to approximately 200 days. As the volume of KOH in the reservoir is increased, the life of the humidifier is increased proportionately. The anode of the getter has a capacity of about 1 amp-hour, which is quite long lived when considering only microamps are generated in the present invention.

Figure 5:
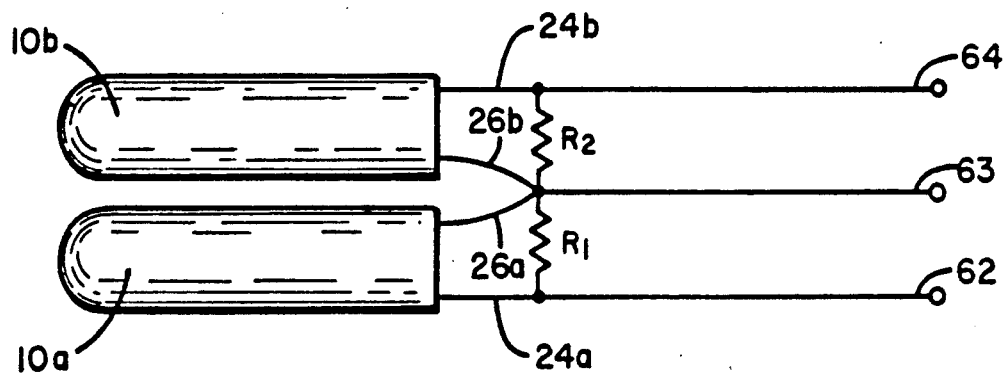
FIG. 5 shows a wiring diagram of the oxygen detector.
Figure 6:
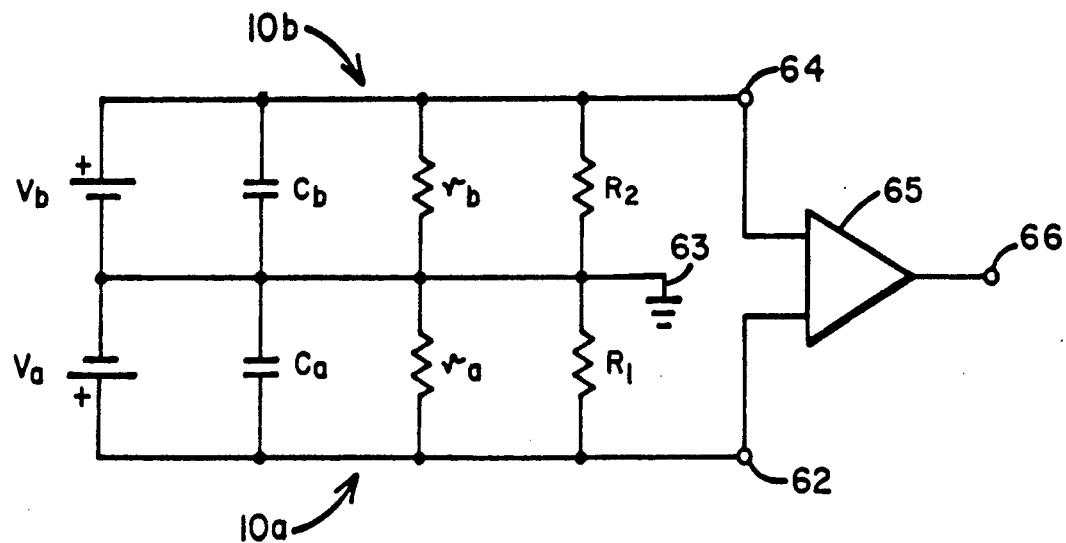
FIG. 6 shows an equivalent schematic diagram of the oxygen detector.

FIGS. 4, 5 and 6 give more details of the gas humidifier device 46 used in association with the oxygen detector 10 of the referenced parent application. Nonetheless, it is believed that other suitable applications for the gas humidifier 46 do exist.

FIG. 4 shows a cross-section view taken along the lines 4—4 of FIG. 3, illustrating some of the electrical and gas connections. Galvanic cell 10a has an external anode wire 26a and an external cathode wire 24a. Galvanic cell 10b has an external anode wire 26b and an external cathode wire 24b. FIG. 5 shows the connections of these wires, wherein anode wires 26a and 26b are connected to intermediate resistors $R_1$ and $R_2$ Cathode wire 24a is connected to a second terminal of resistor $R_1$, and cathode wire 24b is connected to a second terminal of resistor $R_2$. These reconnection points are then brought external of enclosure 34 via common wire 63, "output 1" wire 62, and "output 2" wire 64.

It should be noted that the test gas flow path through the invention is from inlet 42 through humidifier 46, through cell 10a and then through cell 10b, and finally to outlet 60. The cathode elements of the galvanic cells 10a and 10b are electrically connected together to form a common connection, and the anode elements of the cells are each connected across a load resistance to form separate output connections.

FIG. 6 shows an equivalent circuit diagram which illustrates the electrical circuit formed by the oxygen detector 10. The galvanic action which occurs within each cell is respectively represented by $V_a$ and $V_b$; each cell has an equivalent internal capacitance $C_a$ and $C_b$; each cell has an equivalent internal resistance ra and rb, which should be as large as possible. The voltage developed across load resistor $R_1$ is $V_a$, which includes the sum of the galvanic voltage caused by action of the cell in detection of oxygen, and noise voltage caused by the internal cell conditions described earlier herein. Similarly, the voltage developed across load resistance $R_2$ is $V_b$, which includes the sum of the voltage developed by galvanic action of the cell in detecting oxygen plus the noise voltage developed by these same factors. However, the respective noise voltages are subtractive when the voltage is measured between terminals 62 and 64, thereby canceling out any voltage contribution traceable to noise conditions within both galvanic cells. The desired signal response to oxygen detection within the galvanic cells would also appear to be canceled out when measured between terminals 62 and 64, but for the fact that the respective galvanic cells do not equally detect the oxygen content because of their series interconnection. Because the test gas flows first through cell 10a, the oxygen molecules in the test gas are removed from the test gas by virtue of the galvanic cell action which occurs therein, therefore when the test gas is next sequentially passed through the cell 10b there is no galvanic cell action due to oxygen flow within cell 10b. In effect, cell 10b acts solely s a noise generator, generating the equivalent noise signals which are also generated in cell 10a, but these respective noise signals are then coupled in opposing voltage connection to form an output signal which subtractively removes the noise components from the useful portion of the output signal. Terminals 62 and 64 are connected to a differential amplifier 65, which may be of conventional commercial design, and amplifier 65 will produce an output signal at output terminal 66 which is representative of the test gas oxygen content.

If the values of resistances $R_1$ and $R_2$ are each selected to be 10,000 ohms (10 k) and the test gas is passed through the device at a 10 cc per minute flow rate, the useful output signal will be in the microvolt range. In one test under these conditions, the total voltage measured across cell 10a (noise +useful signal) was measured at 100 microvolts, and the total voltage measured across cell 10b (noise) was measured at 75 microvolts. The voltage measured between terminal 62 and 64 was 25 microvolts, which is equivalent to an oxygen permeability measurement of 0.0025 cc per square meter per day (cc/m²/day). In this case, the noise was primarily attributable to a 1° C. change in temperature which occurred during the testing interval.

With the aforementioned load resistors and test conditions, a 1 microvolt change in output voltage, measured between terminals 62 and 64, is equivalent to an oxygen permeability measurement of 0.0001 cc per square meter per day (cc/mphu 2/day); this is approximately a concentration measurement of 36 parts per trillion. therefore, it is apparent that the humidified oxygen detector 10 achieves a measurement sensitivity of at least several orders of magnitude better than any device of the prior art. Further, the large reservoir of electrolyte contained within the device permits a constant control over relative humidity in the test gas, and replenishes water loss which otherwise would occur in the galvanic cells during extended periods of operation.

In operation, it is preferable to construct the reservoir formed by the sealed enclosure 34 nearly filled with KOH. Before actually using the completed assembly for the measurement of a test gas it is preferable to run dry nitrogen gas through the passages for a period of time in order to permit the oxygen which may be trapped inside of enclosure 34, and in solution in KOH, to be removed by the galvanic action of the cell which forms a part of the present invention humidifier 46. After an initial break-in period, which may continue for about a few days in particular applications, the oxygen detector system is then ready for use in measurement of the oxygen content of various test gases. The voltage output at terminal 66 may be calibrated to identify a "zero" reading after this extended break-in period, and thereafter the voltage at terminal 66 may be coupled to a circuit for driving a meter to give a direct readout of oxygen, or alternatively coupled to a circuit for conversion into digital values for processing by a computer. The system will provide accurate readings of oxygen content down to extremely low levels, and the device is usable over an extended life by virtue of the large reservoir of KOH which may be contained within enclosure 34.

The present invention may be embodied in other specific forms and may find other applications without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A device for humidifying a gas without introducing oxygen into the gas to permit subsequent analysis of the humidified gas, comprising:
    a) a liquid reservoir at least partially filled with an electrolyte solution;
    b) a galvanic cell having an anode and a cathode in said reservoir and immersed in said electrolyte solution;
    c) a gas conduit in said reservoir and having an inlet end sealably positioned outside said reservoir, said gas conduit having a portion of its length which is permeable to water but a barrier to electrolytes, said portion being positioned closely adjacent said galvanic cell;
    d) means for introducing said gas into the inlet end of said gas conduit; and
    e) means for electrically interconnecting said anode and said cathode.

2. The device of claim 1, wherein the electrolyte solution includes potassium hydroxide.

3. The device of claim 1, wherein the permeable portion of the gas conduit is positioned closely adjacent the anode.

4. The device of claim 1, wherein the permeable portion of the gas conduit is made from a fluorocarbon copolymer.

5. The device of claim 4, wherein the copolymer is tetrafluoroethylene and vinyl sufonyl fluoride.

6. The device of claim 4, wherein the copolymer is a perfluorianted cation exchange polymer membrane.

7. The device of claim 1, wherein the anode is made from an oxidizable material from the group consisting of: cadmium, arsenic, bismuth, antimony, lead and ferrous hydrate.

8. The device of claim 1, wherein the cathode is made from a reducible material from the group consisting of silver, gold, carbon, graphite, platinum, copper and iridium.

9. The device of claim 1, wherein the anode and cathode are short circuited together.

10. The device of claim 1, wherein the electrolyte solution includes an approximate 12.5 weight percentage solution of potassium hydroxide.

11. A device for humidifying a gas, without introducing oxygen into the gas, to permit subsequent analysis of the humidified gas, comprising:
    (a) an interior anode wrapped with a first wire conductor;
    (b) a gas conduit for passing the gas, having a portion which is permeable to water but a barrier to electrolytes, said gas conduit located adjacent the anode;
    (c) a nonconductive porous diaphragm wrapped about the anode and the permeable conduit portion, being wrapped with a second wire conductor;
    (d) a cathode layer wrapped about the nonconductive porous diaphragm; and
    (e) an enclosure at least partially filled with an electrolyte solution; the anode, the permeable conduit portion, the diaphragm and the cathode being immersed in said electrolyte solution.

12. The device of claim 11, wherein the throttle solution includes potassium hydroxide.

13. The device of claim 11 wherein the first and second wires are electrically interconnected outside the electrolyte solution.

14. The device of claim 11, wherein the permeable portion of the gas conduit is made from a fluorocarbon copolymer.

15. The device of claim 14, wherein the copolymer is tetrafluoroethylene and vinyl sufonyl fluoride.

16. The device of claim 14, wherein the copolymer is a perfluorianted cation exchange polymer membrane.

17. The device of claim 11, wherein the anode is made from an oxidizable material from the group consisting of: cadmium arsenic, bismuth, antimony, lead and ferrous hydrate.

18. The device of claim 11, wherein the cathode is made from a reducible material from the group consisting of silver, gold, carbon, graphite, platinum, copper and iridium,.

19. The device of claim 11, wherein the electrolyte solution includes an approximate 12.5 weight percentage solution of potassium hydroxide.

* * * * *